(12) United States Patent
Jang et al.

(10) Patent No.: US 12,708,460 B2
(45) Date of Patent: Aug. 18, 2026

(54) MICROROBOT AND MICROROBOT SYSTEM

(71) Applicant: IUCF-HYU (INDUSTRY-UNIVERSITY COOPERATION FOUNDATION HANYANG UNIVERSITY), Seoul (KR)

(72) Inventors: Gun Hee Jang, Seoul (KR); Ji Min Park, Seoul (KR); Eunsoo Jung, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 933 days.

(21) Appl. No.: 17/639,091

(22) PCT Filed: Aug. 13, 2020

(86) PCT No.: PCT/KR2020/010752
§ 371 (c)(1),
(2) Date: Feb. 28, 2022

(87) PCT Pub. No.: WO2021/040286
PCT Pub. Date: Mar. 4, 2021

(65) Prior Publication Data

US 2022/0296316 A1 Sep. 22, 2022

(30) Foreign Application Priority Data

Aug. 28, 2019 (KR) ........................ 10-2019-0106035

(51) Int. Cl.
*A61B 34/30* (2016.01)
*A61B 17/00* (2006.01)
(Continued)

(52) U.S. Cl.
CPC .............. *A61B 34/30* (2016.02); *A61B 34/73* (2016.02); *A61B 2017/00345* (2013.01);
(Continued)

(58) Field of Classification Search
CPC .......... A61B 34/73; A61B 2017/00876; A61B 2017/320775; A61B 2034/303;
(Continued)

(56) References Cited

U.S. PATENT DOCUMENTS

2016/0192995 A1* 7/2016 Viswanathan ......... A61B 5/066 606/130
2016/0235491 A1* 8/2016 Choi ...................... A61B 34/30
2017/0027424 A1 2/2017 Ferren et al.

FOREIGN PATENT DOCUMENTS

KR 10-1462588 B1 11/2014
KR 101471526 B1 * 12/2014
(Continued)

OTHER PUBLICATIONS

International Search Report for PCT/KR2020/010752 dated Mar. 9, 2021.
Written Opinion for PCT/KR2020/010752 dated Mar. 9, 2021.

*Primary Examiner* — Carrie R Dorna
*Assistant Examiner* — Julie Thi Tran
(74) *Attorney, Agent, or Firm* — Sughrue Mion, PLLC

(57) ABSTRACT

A microrobot is disclosed. The microrobot comprises: a rotating shaft; a main magnet fixed and coupled to the rotating shaft; a first support body which is inserted into the rotating shaft and which is rotatable around the rotating shaft; a first driving magnet which is fixed and coupled to the first support body and which has a magnetic moment differing, in size, from that of the main magnet; and a plurality of first legs coupled to the outer circumferential surface of the first support body.

9 Claims, 4 Drawing Sheets

(51) Int. Cl.
*A61B 17/3207* (2006.01)
*A61B 34/00* (2016.01)

(52) U.S. Cl.
CPC ............... *A61B 2017/00876* (2013.01); *A61B 2017/320775* (2013.01); *A61B 2034/303* (2016.02)

(58) Field of Classification Search
CPC .......... A61B 34/30; A61B 2017/00345; A61B 2034/731; A61B 17/320758; A61B 2017/00411; A61B 17/22; A61B 34/70; A61M 25/0127; A61M 25/0116; A61M 25/0113; A61M 2025/0177; B25J 7/00; A61N 2/02; A61N 2/06
See application file for complete search history.

(56) References Cited

FOREIGN PATENT DOCUMENTS

| | | | | | |
|---|---|---|---|---|---|
| KR | 101524552 | B1 * | 5/2015 | | |
| KR | 101659367 | B1 * | 9/2016 | | |
| KR | 101772338 | B1 * | 8/2017 | | |
| KR | 101818400 | B1 * | 1/2018 | | |
| WO | WO-2019031678 | A1 * | 2/2019 | ............. | B25J 9/065 |

* cited by examiner 202
30
31
155
121
157
100
115
167
165

MICROROBOT AND MICROROBOT SYSTEM

CROSS REFERENCE TO RELATED APPLICATIONS

This application is a National Stage of International Application No. PCT/KR2020/010752 filed Aug. 13, 2020, claiming priority based on Korean Patent Application No. 10-2019-0106035 filed Aug. 28, 2019.

TECHNICAL FIELD

The present invention relates to a microrobot, and more particularly, to a microrobot that is movable under the control of an external rotating magnetic field, and a microrobot system including the microrobot.

BACKGROUND ART

A conventional method of treating a vascular disease is performed by inserting a catheter through a femoral artery, dilating a blood vessel through a manual operation of a doctor, and installing an instrument that may maintain the dilated blood vessel, and such a method is referred to as coronary angioplasty. However, it is difficult to apply the catheter to complex blood vessels due to structural characteristics thereof, and the success of a procedure tends to be affected greatly by the skill of the doctor.

Recently, researches on a microrobot for a vascular treatment that may be wirelessly operated have been actively conducted by various advanced research institutes as a method to overcome such a disadvantage of the catheter. Although a structure in which a flexible leg is added to a microrobot has been developed to ensure stability and improve mobility when driven in a pulsating flow or performing drilling, the leg may cause damage to a blood vessel when rotating at a high speed.

DISCLOSURE

Technical Problem

The present invention provides a microrobot capable of minimizing damage to an inner wall of a blood vessel.

In addition, the present invention provides a microrobot capable of improving accuracy of a treatment by stably performing a drilling process.

Technical Solution

According to the present invention, a microrobot includes: a rotating shaft; a main magnet fixedly coupled to the rotating shaft; a first support body fitted around the rotating shaft, and rotatable about the rotating shaft; a first driving magnet fixedly coupled to the first support body, and having a magnetic moment having a magnitude that is different from a magnitude of a magnetic moment of the main magnet; and a plurality of first legs coupled to an outer circumferential surface of the first support body.

In addition, the main magnet may have the magnetic moment that is greater than the magnetic moment of the first driving magnet.

In addition, the microrobot may further include: a second support body fitted around the rotating shaft on an opposite side of the first support body with the main magnet interposed between the first support body and the second support body, and rotatable about the rotating shaft; a second driving magnet fixedly coupled to the second support body, and having a magnetic moment having a magnitude that is different from a magnitude of the magnetic moment of the main magnet; and a plurality of second legs coupled to an outer circumferential surface of the second support body.

In addition, the main magnet may have the magnetic moment that is greater than the magnetic moment of the second driving magnet.

In addition, the second driving magnet may have the magnetic moment having the magnitude that is equal to the magnitude of the magnetic moment of the first driving magnet.

In addition, the main magnet may include a cylindrical magnet, and may be configured such that an N-pole and an S-pole are arranged opposite to each other with the rotating shaft interposed therebetween.

In addition, the microrobot may further include a drill tip fixedly coupled to a front end of the rotating shaft, and configured to rotate integrally with the rotating shaft.

According to the present invention, a microrobot system includes: a microrobot in which a main magnet is fixedly coupled to a rotating shaft, a first support body having an outer circumferential surface to which a plurality of legs are coupled is coupled integrally with a first driving magnet so as to be fitted around the rotating shaft, and the first support body and the first driving magnet are rotatable about the rotating shaft; and a magnetic field generation unit configured to generate an external rotating magnetic field on an outside of the microrobot, wherein the main magnet and the first driving magnet have magnetic moments having mutually different magnitudes.

In addition, the microrobot may include a second support body and a second driving magnet, which are fitted around the rotating shaft on an opposite side of the first support body with the main magnet interposed between the first support body and the second support body and the second driving magnet, and coupled integrally with each other so as to be rotatable about the rotating shaft, and the second driving magnet may have a magnetic moment having a magnitude that is different from the magnitude of the magnetic moment of the main magnet.

In addition, the magnetic field generation unit may include: a first mode for generating an external rotating magnetic field having a frequency that is smaller than a step-out frequency of each of the main magnet and the first driving magnet; and a second mode for generating an external rotating magnetic field having a frequency that is smaller than the step-out frequency of the main magnet and larger than the step-out frequency of the first driving magnet.

Advantageous Effects

According to the present invention, in the first mode, the microrobot may move with a propulsion force generated from legs as a treatment unit and a driving unit rotate together with each other at a low speed, and in the second mode, the drilling process may be performed as the rotation of the driving unit is minimized and the treatment unit rotates at a high speed, so that the damage to the inner wall of the blood vessel can be minimized.

In addition, in the second mode, the drilling process may be performed while the leg of the driving unit is supported on the inner wall of the blood vessel so as to stably locate a rotating shaft of the treatment unit, so that the accuracy of the treatment can be increased.

BEST MODE

Figure 1:
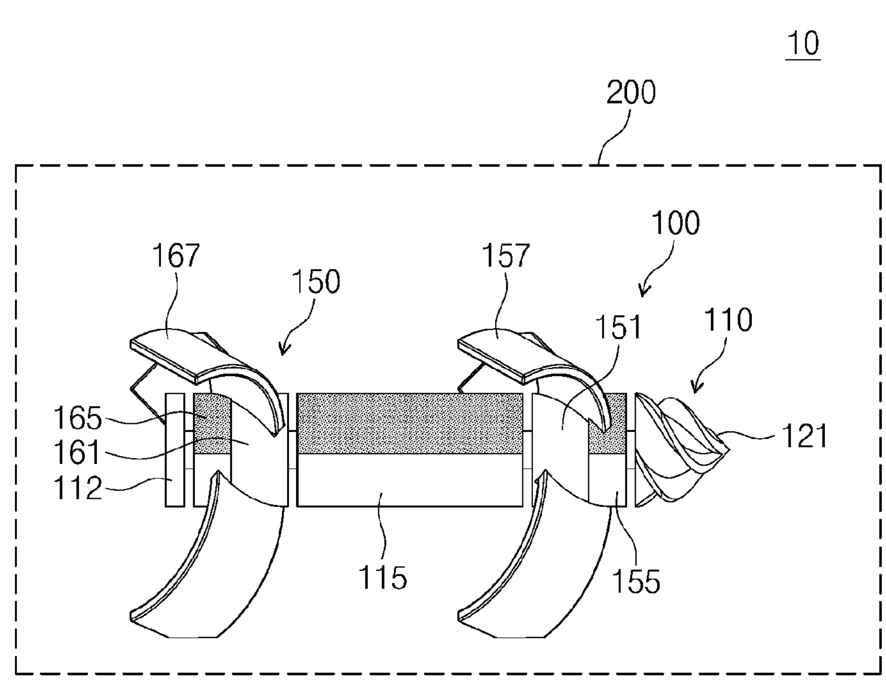
FIG. 1 is a view showing a microrobot system according to an embodiment of the present invention.

According to the present invention, a microrobot includes: a rotating shaft; a main magnet fixedly coupled to the rotating shaft; a first support body fitted around the rotating shaft, and rotatable about the rotating shaft; a first driving magnet fixedly coupled to the first support body, and having a magnetic moment having a magnitude that is different from a magnitude of a magnetic moment of the main magnet; and a plurality of first legs coupled to an outer circumferential surface of the first support body.

Mode for Invention

Hereinafter, exemplary embodiments of the present invention will be described in detail with reference to the accompanying drawings. However, the technical idea of the present invention is not limited to the embodiments described herein, but may be realized in different forms. The embodiments introduced herein are provided to sufficiently deliver the idea of the present invention to those skilled in the art so that the disclosed contents may become thorough and complete.

When it is mentioned in the present disclosure that one element is on another element, it means that one element may be directly formed on another element, or a third element may be interposed between one element and another element. Further, in the drawings, thicknesses of films and areas are exaggerated for efficient description of the technical contents.

In addition, in the various embodiments of the present disclosure, the terms such as first, second, and third are used to describe various elements, but the elements are not limited to the terms. The terms are used only to distinguish one element from another element. Therefore, an element mentioned as a first element in one embodiment may be mentioned as a second element in another embodiment. The embodiments described and illustrated herein include their complementary embodiments. Further, the term “and/or” used herein is used to include at least one of the elements enumerated before and after the term.

As used herein, the terms of a singular form may include plural forms unless the context clearly indicates otherwise. Further, the terms such as “including” and “having” are used to designate the presence of features, numbers, steps, elements, or combinations thereof described in the present disclosure, and shall not be construed to preclude any possibility of the presence or addition of one or more other features, numbers, steps, elements, or combinations thereof. In addition, the term “connection” used herein is used to include both indirectly and directly connecting a plurality of elements.

Further, in the following description of the present invention, detailed descriptions of known functions and configurations incorporated herein will be omitted when they may make the subject matter of the present invention unnecessarily unclear.

Figure 2:
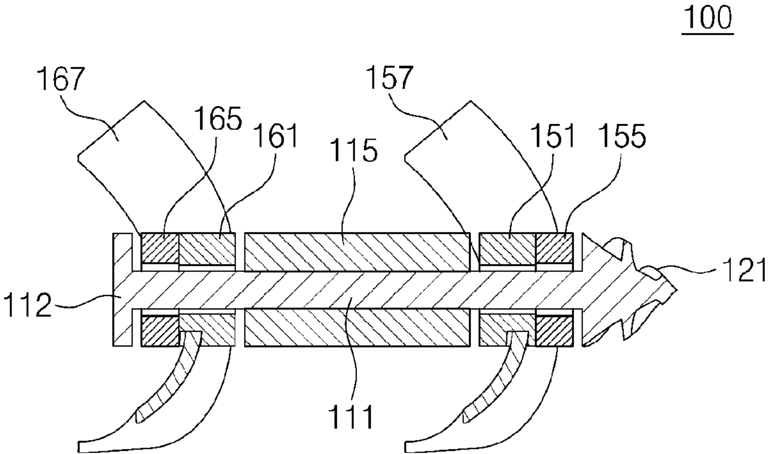
FIG. 2 is a sectional view showing a microrobot of FIG. 1.

FIG. 1 is a view showing a microrobot system according to an embodiment of the present invention, and FIG. 2 is a sectional view showing a microrobot of FIG. 1.

Referring to FIGS. 1 and 2, a microrobot system 10 may include a microrobot 100 and a magnetic field generation unit 200.

The microrobot 100 may perform movement and drilling processes in various fluid environments such as tubular tissue in a human body and industrial piping. The microrobot 100 provided for a treatment of a blood vessel in a human body according to the present invention will be described for illustrative purposes.

The magnetic field generation unit 200 may generate an external rotating magnetic field from an outside of the microrobot 100. The magnetic field generation unit 200 may generate the external rotating magnetic field from an outside of a patient into which the microrobot 100 is inserted. The magnetic field generation unit 200 may generate the external rotating magnetic field at frequencies having various magnitudes.

The microrobot 100 may include a treatment unit 110 and a driving unit 150. The treatment unit 110 may performs a drilling process, and the driving unit 150 may generate a propulsion force that allows the microrobot 100 to move.

The treatment unit 110 may include a rotating shaft 111, a main magnet 115, and a drill tip 121.

The rotating shaft 111 may have a rod shape having a predetermined length, and may be formed of a non-magnetic material. A latching sill 112 may be formed at a rear end of the rotating shaft 111. The latching sill 112 may prevent the driving unit 150 from being separated.

The main magnet 115 may be a magnet having a cylindrical shape, and may have an inner space into which the rotating shaft 111 is inserted and fixed. The main magnet 115 may be configured such that an N-pole and an S-pole are arranged opposite to each other with the rotating shaft interposed therebetween.

The drill tip 121 may be fixedly coupled to a front end of the rotating shaft 111. The drill tip 121 may be formed on an outer circumferential surface thereof with a spiral protrusion for the drilling process. The drill tip 121 may prevent the driving unit 150 from being separated.

The driving unit 150 may include a first support body 151, a first driving magnet 155, a first leg 157, a second support body 161, a second driving magnet 165, and a second leg 167.

The first support body 151 may have a cylindrical shape, and the rotating shaft 111 may be inserted into the first support body 151. The first support body 151 may be located between the main magnet 115 and the drill tip 121. The first support body 151 may be relatively rotatable about the rotating shaft 111. The first support body 151 may be formed of a non-magnetic material.

The first driving magnet 155 may have a cylindrical shape having the same diameter as the first support body 151, and may be coupled integrally with the first support body 151. The first driving magnet 155 may be located between the first support body 151 and the drill tip 121. The magnetic coupling of the first driving magnet 155 with the main magnet 115 may be blocked by the first support body 151. The rotating shaft 111 may be inserted into the first driving magnet 155. The first driving magnet 155 may be relatively rotatable about the rotating shaft 111, integrally with the first support body 151. The first driving magnet 155 may have a magnetic moment having a magnitude that is different from a magnitude of a magnetic moment of the main magnet 115. According to an embodiment, the first driving magnet 155 may have a magnetic moment having a magnitude that is smaller than the magnitude of the magnetic moment of the main magnet 115.

A plurality of first legs 157 may be spaced apart from each other along a circumference of an outer circumferential surface of the first support body 151, and one end of the first leg 157 may be coupled to the first support body 151. The first leg 157 may have a rectangular plate shape having a thin thickness, and may be formed of a flexible material. According to the embodiment, three first legs 157 may be provided along a circumference of the first support body 151.

The second support body 161 may have a cylindrical shape, and the rotating shaft 111 may be inserted into the second support body 161. The second support body 161 may be located on an opposite side of the first support body 151 with respect to the main magnet 115. The second support body 161 may be located between the main magnet 115 and the latching sill 112. The second support body 161 may be formed in the same shape as the first support body 151, and formed of the same material as the first support body 151.

The second driving magnet 165 may have a cylindrical shape having the same diameter as the second support body 161, and may be coupled integrally with the second support body 161. The second driving magnet 165 may be located between the second support body 161 and the latching sill 112. The magnetic coupling of the second driving magnet 165 with the main magnet 115 may be blocked by the second support body 161. The rotating shaft 111 may be inserted into the second driving magnet 165. The second driving magnet 165 may be relatively rotatable about the rotating shaft 111, integrally with the second support body 161. The second driving magnet 165 may have a magnetic moment having a magnitude that is different from the magnitude of the magnetic moment of the main magnet 115. The second driving magnet 165 may have a magnetic moment having a magnitude that is smaller than the magnitude of the magnetic moment of the main magnet 115. The second driving magnet 165 may have a magnetic moment having a magnitude that is equal to the magnitude of the magnetic moment of the first driving magnet 155.

A plurality of second legs 167 may be spaced apart from each other along a circumference of an outer circumferential surface of the second support body 161, and one end of the second leg 167 may be coupled to the second support body 161. The second leg 167 may have a rectangular plate shape having a thin thickness, and may be formed of a flexible material. According to the embodiment, three second legs 167 may be provided along a circumference of the second support body 161.

Hereinafter, an operation process of the microrobot 100 through the magnetic field generation unit 200 will be described.

A magnetic torque applied to the magnets 115, 155, and 165 of the microrobot 100 within an external magnetic field may be expressed by the following formula.

$$T=m\times B \qquad \text{Formula (1)}$$

In this case, T is a magnetic torque formed in a magnet by an external magnetic field, m is a magnetic moment of a magnet, and B is strength of an external magnetic field. From Formula (1), an external rotating magnetic field for generating a rotational motion of the microrobot 100 may be expressed by the following Formula (2).

$$B_{ERMF}(t)=B_0(0, \cos 2\pi ft, \sin 2\pi ft) \qquad \text{Formula (2)}$$

In this case, $B_0$ is strength of an external rotating magnetic field, f is a frequency of an external rotating magnetic field, and t is a time.

According to Formula (2) described above, the rotational motion of the microrobot 100 may be generated by using the external rotating magnetic field.

Meanwhile, when a magnitude of a rotation frequency of the external magnetic field is increased, the step-out in which the rotational motion of the microrobot 100 is not synchronized with the external rotating magnetic field may occur. Since a frequency at which the step-out occurs is proportional to the magnetic moment of each of the magnets 115, 155, and 165, the treatment unit 110 may have a large step-out frequency due to the main magnet 115 having a relatively large magnetic moment, and the driving unit 150 may have a small step-out frequency due to the driving magnets 155 and 165 having a relatively small magnetic moment. Therefore, a selective rotational motion of the driving unit 150 may be generated by adjusting the frequency of the external rotating magnetic field.

The step-out frequency may be expressed by the following Formula (3).

$$\omega=\|m\|\|B\|/c \qquad (3)$$

In this case, ω is a step-out frequency, and c is a drag coefficient, which varies according to surface friction, fluid viscosity, a robot shape, and the like.

The treatment unit 110 and the driving unit 150 may have step-out frequencies having mutually different magnitudes depending on a difference of the magnetic moments. Therefore, the magnetic field generation unit 200 may generate selective rotational motions of the treatment unit 110 and the driving unit 150 by adjusting the frequency of the external rotating magnetic field.

Figure 3:
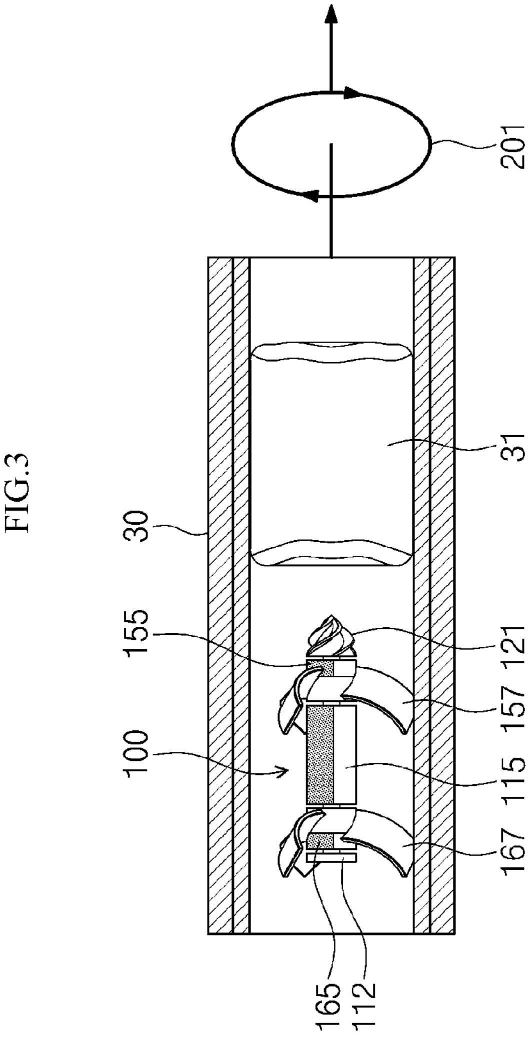
FIGS. 3 and 4 are views showing rotational motions of a treatment unit and a driving unit according to a frequency of an external rotating magnetic field.
Figure 4:
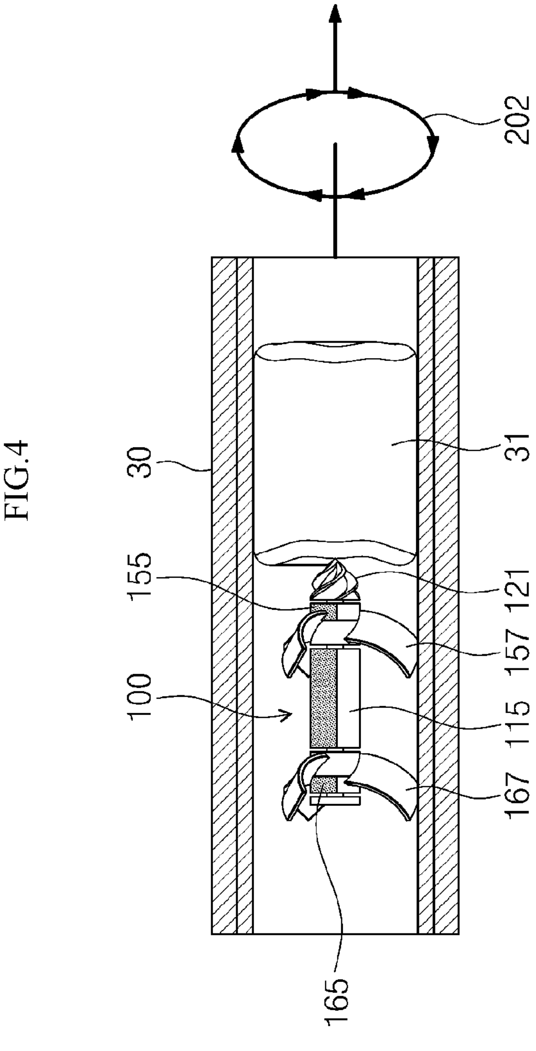

FIGS. 3 and 4 are views showing rotational motions of a treatment unit and a driving unit according to a frequency of an external rotating magnetic field.

First, referring to FIG. 3, the magnetic field generation unit 200 may include a first mode for generating an external rotating magnetic field 201 having a frequency that is smaller than a step-out frequency of each of the main magnet 115 and the first and second driving magnets 155 and 165.

When the magnetic field generation unit 200 generates the external rotating magnetic field 201 having the frequency that is smaller than the step-out frequency of each of the main magnet 115 and the first and second driving magnets 155 and 165, both the treatment unit 110 and the driving unit 150 may be aligned in a magnetic field direction to generate the rotational motions. Due to the rotational motion of the driving unit 150, the flexible legs 157 and 167 may rotate to generate a propulsion force within a blood vessel 30, so that the microrobot 100 may move.

Referring to FIG. 4, the magnetic field generation unit 200 may include a second mode for generating an external rotating magnetic field 202 having a frequency that is smaller than the step-out frequency of the main magnet 115 and larger than the step-out frequency of each of the first and second drive magnets 155 and 165.

When the magnetic field generator 200 generates a frequency of the external rotating magnetic field 202 that is smaller than the step-out frequency of the main magnet 115 and greater than the step-out frequency of the first and second class magnets 155 and 165, the driving unit 150 may not be synchronized with the external rotating magnetic field 202 so that the rotation of the driving unit 150 may be minimized, and only the treatment unit 110 may generate the rotational motion. Due to the rotational motion of the treatment unit 110, the drill tip 121 may perform the drilling process on a lesion part 31. In this case, since the legs 157 and 167 of the driving unit 150 are supported on an inner wall of the blood vessel 30, a position of the drill tip 121 and the rotating shaft 111 may be fixed, so that accuracy of the treatment may be increased, and damage to the inner wall of the blood vessel 30 may be minimized.

Although the exemplary embodiments of the present invention have been described in detail, the scope of the present invention is not limited to a specific embodiment, and should be interpreted by the appended claims. In addition, it should be understood by those of ordinary skill in the art that various changes and modifications can be made without departing from the scope of the present invention.

INDUSTRIAL APPLICABILITY

The microrobot and the microrobot system including the same according to the present invention may treat a vascular disease.

The invention claimed is:

1. A microrobot comprising:

a rotating shaft;

a main magnet fixedly coupled to the rotating shaft;

a first support body fitted around the rotating shaft, and rotatable about the rotating shaft;

a first driving magnet fixedly coupled to the first support body, and having a magnetic moment having a magnitude that is different from a magnitude of a magnetic moment of the main magnet; and a plurality of first legs coupled to an outer circumferential surface of the first support body, wherein, in a first mode in which an external rotating magnetic field having a frequency lower than a step-out frequency of the main magnet and a step-out frequency of the first driving magnet applied, the main magnet and the first driving magnet are aligned in a direction of the external rotating magnetic field and rotate together, and wherein, in a second mode in which an external rotating magnetic field having a frequency lower than the step-out frequency of the main magnet but higher than the step-out frequency of the first driving magnet applied, the first driving magnet rotates less than in the first mode, and the main magnet rotates in synchronization with the external rotating magnetic field.

2. The microrobot of claim 1, wherein the main magnet has the magnetic moment that is greater than the magnetic moment of the first driving magnet.

3. The microrobot of claim 1, further comprising:

a second support body fitted around the rotating shaft on an opposite side of the first support body with the main magnet interposed between the first support body and the second support body, and rotatable about the rotating shaft;

a second driving magnet fixedly coupled to the second support body, and having a magnetic moment having a magnitude that is different from a magnitude of the magnetic moment of the main magnet; and a plurality of second legs coupled to an outer circumferential surface of the second support body.

4. The microrobot of claim 3, wherein the magnetic moment of the main magnet is greater than the magnetic moment of the second driving magnet.

5. The microrobot of claim 3, wherein the magnitude of the magnetic moment of the second driving magnet is equal to the magnitude of the magnetic moment of the first driving magnet.

6. The microrobot of claim 1, wherein the main magnet includes a cylindrical magnet, and is configured such that an N-pole and an S-pole are arranged opposite to each other with the rotating shaft interposed therebetween.

7. The microrobot of claim 1, further comprising a drill tip fixedly coupled to a front end of the rotating shaft, and configured to rotate integrally with the rotating shaft.

8. A microrobot system comprising:

a microrobot in which a main magnet is fixedly coupled to a rotating shaft, a first support body having an outer circumferential surface to which a plurality of legs is coupled integrally with a first driving magnet so as to be fitted around the rotating shaft, and the first support body and the first driving magnet are rotatable about the rotating shaft; and a magnetic field generator configured to generate an external rotating magnetic field on an outside of the microrobot, wherein the main magnet and the first driving magnet have magnetic moments having different magnitudes, wherein, in a first mode in which the external rotating magnetic field having a frequency lower than a step-out frequency of the main magnet and a step-out frequency of the first driving magnet applied, the main magnet and the first driving magnet are aligned in a direction of the external rotating magnetic field and rotate together, and wherein, in a second mode in which the external rotating magnetic field having a frequency lower than the step-out frequency of the main magnet but higher than the step-out frequency of the first driving magnet is applied, the first driving magnet rotates less than in the first mode, and the main magnet rotates in synchronization with the external rotating magnetic field.

9. The microrobot system of claim 8, wherein the microrobot includes a second support body and a second driving magnet, which are fitted around the rotating shaft on an opposite side of the first support body with the main magnet interposed between the first support body and the second support body and the second driving magnet, and coupled integrally with each other so as to be rotatable about the rotating shaft, and the second driving magnet has a magnetic moment having a magnitude that is different from the magnitude of the magnetic moment of the main magnet.

* * * * *